US00PP26390P2

(12) United States Plant Patent
Dummen

(10) Patent No.: US PP26,390 P2
(45) Date of Patent: Feb. 2, 2016

(54) ***CALIBRACHOA* PLANT NAMED 'DUEHULOR'**

(50) Latin Name: ***Calibrachoa* sp.**
Varietal Denomination: Duehulor

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 14/120,823

(22) Filed: Jul. 1, 2014

(51) Int. Cl.
*A01H 5/02* (2006.01)

(52) U.S. Cl.
USPC ..... Plt./413

(58) Field of Classification Search
USPC ..... Plt./413
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Calibrachoa* plant named 'Duehulor', characterized by its compact, semi-upright and outwardly spreading to trailing and decumbent plant habit; freely branching habit; early and freely flowering habit; large orange-colored flowers with dark purple-colored centers and venation; and good garden performance.

1 Drawing Sheet

Botanical designation: *Calibrachoa* sp.
Cultivar denomination: 'DUEHULOR'.

CROSS REFERENCED TO CLOSELY-RELATED APPLICATIONS

Title: *Calibrachoa* Plant Named 'Duehulgo'
Applicant: Tobias Dümmen
Filed: Concurrently with this application, U.S. Plant patent application Ser. No. 14/120,826

BACKGROUND OF THE INVENTION

The present invention relates to a new and distinct cultivar of *Calibrachoa* plant, botanically known as *Calibrachoa* sp. and hereinafter referred to by the name 'Duehulor'.

The new *Calibrachoa* plant is a product of a planned breeding program conducted by the Inventor in Rheinberg, Germany. The objective of the breeding program is to create new compact *Calibrachoa* plants with large attractive flowers.

The new *Calibrachoa* plant originated from a cross-pollination made by the Inventor in July, 2011 in Rheinberg, Germany of a proprietary selection of *Calibrachoa* sp. identified as code number A08-5398-009, not patented, as the female, or seed, parent with a proprietary selection of *Calibrachoa* sp. identified as code number F-019-0202, not patented, as the male, or pollen, parent. The new *Calibrachoa* plant was discovered and selected by the Inventor as a single flowering plant from within the progeny of the stated cross-pollination in a controlled greenhouse environment in Rheinberg, Germany in May, 2013.

Asexual reproduction of the new *Calibrachoa* plant by vegetative terminal cuttings in a controlled greenhouse environment in Rheinberg, Germany since June, 2013 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duehulor'. These characteristics in combination distinguish 'Duehulor' as a new and distinct *Calibrachoa* plant:

1. Compact, semi-upright and outwardly spreading to trailing and decumbent plant habit.
2. Freely branching habit.
3. Early and freely flowering habit.
4. Large orange-colored flowers with dark purple-colored centers and venation.
5. Good garden performance.

The new *Calibrachoa* can be compared to plants of the female parent selection. Plants of the new *Calibrachoa* differ primarily from plants of the female parent selection in plant habit as plants of the new *Calibrachoa* are more compact than plants of the female parent selection. In addition, plants of the new *Calibrachoa* have smaller flowers than plants of the female parent selection and differ in flower color.

The new *Calibrachoa* can be compared to plants of the male parent selection. Plants of the new *Calibrachoa* differ primarily from plants of the male parent selection in flower color as plants of the male parent selection have very dark purple-colored flowers. In addition, plants of the new *Calibrachoa* have larger flowers than plants of the male parent selection.

Plants of the new *Calibrachoa* can be compared to plants of 'Duehulgo', disclosed in U.S. Plant patent application Ser. No. 14/120,826, filed concurrently. Plants of the new *Calibrachoa* and 'Duehulgo' differ primarily in flower color.

Plants of the new *Calibrachoa* can also be compared to plants of *Calibrachoa* sp. 'USCALI413-8', disclosed in U.S. Plant Pat. No. 19,843. In side-by-side comparisons, plants of the new *Calibrachoa* differed primarily from plants of 'USCALI413-8' in the following characteristics:

1. Plants of the new *Calibrachoa* were more compact than plants of 'USCALI413-8'.
2. Plants of the new *Calibrachoa* had smaller leaves than plants of 'USCALI413-8'.
3. Plants of the new *Calibrachoa* had slightly smaller flowers than plants of 'USCALI413-8'.
4. Plants of the new *Calibrachoa* and 'USCALI413-8' differed in flower color as plants of 'USCALI413-8' had darker-colored flowers.

BRIEF DESCRIPTION OF THE PHOTOGRAPH

The accompanying colored photograph illustrates the overall appearance of the new *Calibrachoa* plant showing the colors as true as it is reasonably possible to obtain in colored reproductions of this type. Colors in the photograph may differ slightly from the color values cited in the detailed botanical description which accurately describe the colors of the new *Calibrachoa* plant.

The photograph is a side perspective view of a typical flowering plant of 'Duehulor' grown in a container.

DETAILED BOTANICAL DESCRIPTION

The aforementioned photograph and following observations, measurements and values describe plants grown during the summer in 30-cm containers in a glass-covered greenhouse in Rheinberg, Germany and under cultural practices typical of commercial *Calibrachoa* production. During the production of the plants, day and night temperatures averaged 18° C. and light levels averaged 4,500 lux. Rooted young plants were pinched one time three weeks after planting and were 13 weeks old when the photograph and description were taken. In the following description, color references are made to The Royal Horticultural Society Colour Chart, 2007 Edition, except where general terms of ordinary dictionary significance are used.

Botanical classification: *Calibrachoa* sp. 'Duehulor'.

Parentage:

*Female, or seed, parent.*—Proprietary selection of *Calibrachoa* sp. identified as code number A08-5398-009, not patented.

*Male, or pollen, parent.*—Proprietary selection of *Calibrachoa* sp. identified as code number F-019-0202, not patented.

Propagation:

*Type.*—By vegetative cuttings.

*Time to initiate roots, summer.*—About five days at temperatures about 20° C.

*Time to initiate roots, winter.*—About seven days at temperatures about 20° C.

*Time to produce a rooted young plant, summer.*—About three weeks at temperatures about 20° C.

*Time to produce a rooted young plant, winter.*—About four weeks at temperatures about 20° C.

*Root description.*—Fine, fibrous; white in color.

*Rooting habit.*—Freely branching; dense.

Plant description:

*Plant and growth habit.*—Compact, semi-upright and outwardly spreading to trailing and decumbent plant habit; freely branching habit with about eight primary lateral branches developing per plant; pinching enhances branching; vigorous growth habit; moderate growth rate.

*Plant height.*—About 28 cm.

*Plant diameter.*—About 77 cm.

Lateral branch description:

*Length.*—About 30 cm.

*Diameter.*—About 4 mm.

*Internode length.*—About 1.8 cm.

*Strength.*—Strong.

*Aspect.*—Initially upright to outwardly spreading to trailing and decumbent.

*Texture.*—Pubescent.

*Color.*—Close to 146B.

Leaf description:

*Arrangement.*—Alternate, simple.

*Length.*—About 2.1 cm.

*Width.*—About 5 mm.

*Shape.*—Oblanceolate.

*Apex.*—Rounded.

*Base.*—Cuneate.

*Margin.*—Entire.

*Texture, upper and lower surfaces.*—Pubescent.

*Venation pattern.*—Pinnate; arcuate.

*Color.*—Developing leaves, upper surface: Close to 137D. Developing leaves, lower surface: Close to 138A. Fully expanded leaves, upper surface: Close to 137C; venation, close to 137D. Fully expanded leaves, lower surface: Close to 137D; venation, close to 137D.

*Petioles.*—Length: About 2.4 mm. Diameter: About 0.9 mm. Texture, upper and lower surfaces: Pubescent. Color, upper and lower surfaces: Close to 146C.

Flower description:

*Flower arrangement and habit.*—Single salverform flowers arising from leaf axils; freely flowering habit with usually about 125 to 145 flowers developing per plant; flowers face upright or outwardly.

*Fragrance.*—None detected.

*Natural flowering season.*—Early flowering habit, plants of the new *Calibrachoa* initiate and develop flowers about four to five weeks after planting; plants flower continuously from the spring throughout the summer in Germany.

*Flower longevity.*—Individual flowers last about seven to ten days on the plant; flowers not persistent.

*Flower diameter.*—About 3.2 cm.

*Flower length (height).*—About 3.2 cm.

*Flower throat diameter.*—About 7.6 mm.

*Flower tube length.*—About 1.4 cm.

*Flower tube diameter, base.*—About 7.6 mm.

*Flower buds.*—Length: About 2.4 cm. Diameter: About 5.2 mm. Shape: Elongated oblong. Color: Close to 178D.

*Corolla.*—Arrangement: Five petals fused at the base and opening into a flared trumpet. Petal length from throat: About 2.8 cm. Petal lobe width: About 1.6 cm. Petal shape: Roughly spatulate. Petal apex: Mostly rounded to slightly retuse. Petal margin: Entire. Petal texture, upper and lower surfaces: Smooth, glabrous. Throat texture: Smooth, glabrous. Tube texture: Smooth, glabrous. Color: Petal, when opening, upper surface: Close to 178D; towards the base, close to 185B. Petal, when opening, lower surface: Close to 180C. Petal, fully opened, upper surface: Close to 167C; towards the base and venation, close to 185B; main color becoming closer to 162C with development. Petal, fully opened, lower surface: Close to 170D; venation, close to 185A. Throat: Close to 163B; venation, close to 181B. Tube: Close to 163B; venation, close to 181B.

*Calyx.*—Arrangement: Star-shaped calyx with five sepals; sepals fused at the base. Sepal length: About 1.1 cm. Sepal width: About 2.6 mm. Sepal shape: Lanceolate. Sepal apex: Acute. Sepal margin: Entire. Sepal texture, upper and lower surfaces: Pubescent. Color, upper surface: Close to 146A. Color, lower surface: Close to 146B.

*Peduncles.*—Length: About 1.2 cm. Diameter: About 1 mm. Angle: About 45° from stem axis. Strength: Moderately strong. Texture: Pubescent. Color: Close to 144B.

Reproductive organs:

*Stamens.*—Quantity: Six per flower. Filament length: About 6.2 mm. Filament color: Close to 150B. Anther shape: Ellipsoidal. Anther length: About 0.4 mm. Anther color: Close to 163C. Pollen amount: Scarce. Pollen color: Close to 163B.

*Pistils.*—Quantity: One per flower. Pistil length: About 9 mm. Style length: About 8 mm. Style color: Close to 144D. Stigma shape: Ellipsoidal. Stigma color: Close to 144A. Ovary color: Close to N144C.

*Seeds and fruits.*—Seed and fruit development have not been observed on plants of the new *Calibrachoa.*

Garden performance: Plants of the new *Calibrachoa* have been observed to have good garden performance and tolerate wind, rain and temperatures ranging from about 5° C. to about 40° C.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'Duehulor' as illustrated and described.

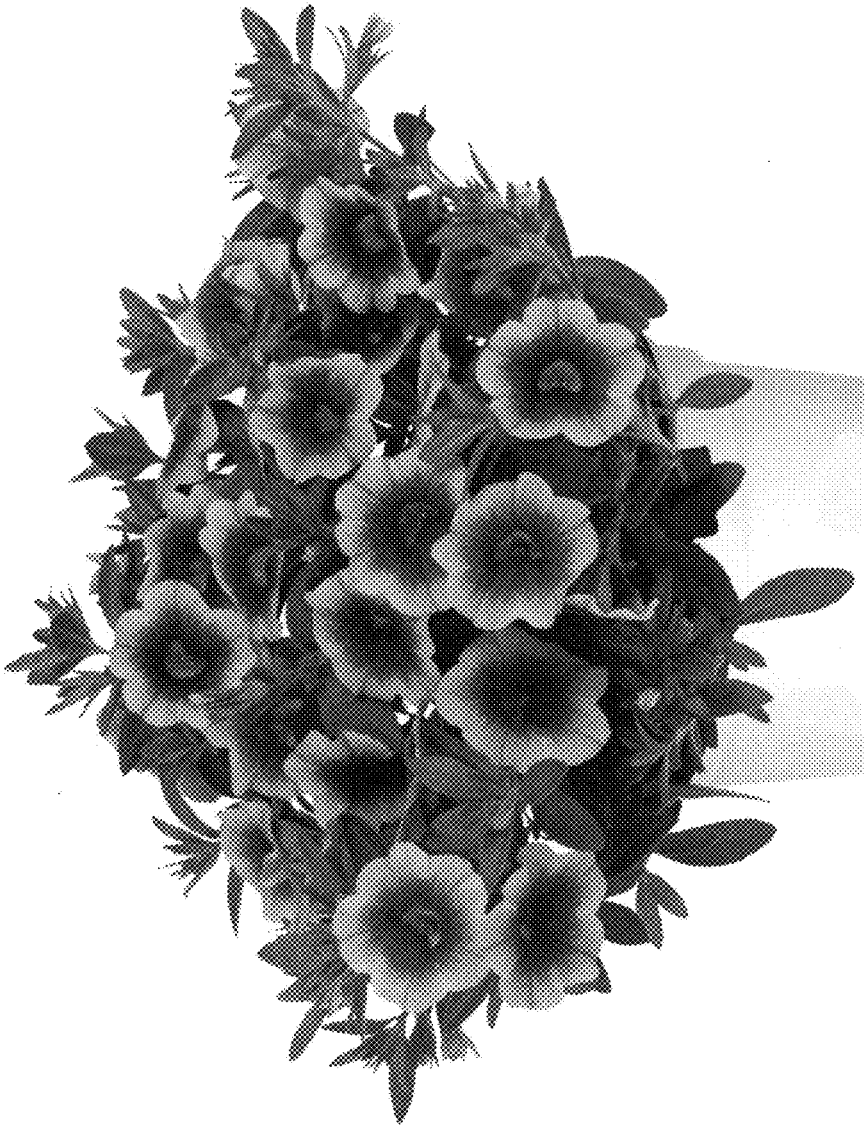

* * * * *